United States Patent
Fabian et al.

(10) Patent No.: US 7,787,931 B2
(45) Date of Patent: Aug. 31, 2010

(54) PORTABLE SURGICAL IMPLEMENT DETECTOR

(76) Inventors: Carl E. Fabian, 577 NE. 96th St., Miami Shores, FL (US) 33138; Philip M. Anderson, III, 37 Winding Way, Madison, NJ (US) 07940

( * ) Notice: Subject to any disclaimer, the term of this patent is extended or adjusted under 35 U.S.C. 154(b) by 2381 days.

(21) Appl. No.: 10/307,029

(22) Filed: Dec. 2, 2002

(65) Prior Publication Data
US 2003/0105394 A1   Jun. 5, 2003

(51) Int. Cl.
*A61B 5/05* (2006.01)
(52) U.S. Cl. .................. 600/424; 600/407; 600/409; 340/540; 340/573.1
(58) Field of Classification Search ........... 600/407, 600/409, 424; 340/540, 573.1
See application file for complete search history.

(56) References Cited

U.S. PATENT DOCUMENTS

| | | | |
|---|---|---|---|
| 2,740,405 A | 4/1956 | Riordan | 128/296 |
| 3,422,816 A | 1/1969 | Robinson et al. | 128/296 |
| 3,587,583 A * | 6/1971 | Greenberg | 604/362 |
| 4,114,601 A | 9/1978 | Abels | 128/1 R |
| 4,510,489 A | 4/1985 | Anderson et al. | 340/572 |
| 4,710,752 A * | 12/1987 | Cordery | 340/551 |
| 5,057,095 A * | 10/1991 | Fabian | 604/362 |
| 5,105,829 A | 4/1992 | Fabian et al. | 128/899 |
| 5,107,862 A | 4/1992 | Fabian et al. | 128/899 |
| 5,188,126 A | 2/1993 | Fabian et al. | 128/899 |
| 5,190,059 A | 3/1993 | Fabian et al. | 128/899 |
| 5,329,944 A | 7/1994 | Fabian et al. | 128/899 |
| 5,456,718 A | 10/1995 | Szymaitis | 128/889 |
| 6,366,206 B1 * | 4/2002 | Ishikawa et al. | 340/573.1 |
| 6,474,341 B1 * | 11/2002 | Hunter et al. | 128/899 |
| 2002/0193685 A1 * | 12/2002 | Mate et al. | 600/424 |

FOREIGN PATENT DOCUMENTS

| | | |
|---|---|---|
| FR | 2580172 | 10/1986 |
| GB | 1274 061 | 5/1972 |
| WO | WO 9417767 | 7/1998 |

* cited by examiner

*Primary Examiner*—Brian Casler
*Assistant Examiner*—James Kish
(74) *Attorney, Agent, or Firm*—Ernest D. Buff & Associates, LLC; Ernest D. Buff

(57) ABSTRACT

Surgical implements used during an operating procedure are detected in human or animal tissue. Markers attached to the surgical implements change their impedance at a preselected frequency in the presence of an electromagnetic field. Each of the markers is thereby provided with signal-identifying characteristics. The signal-identifying characteristics are detected by a freely movable, portable detection unit from a first location proximate the patient in an accurate, reliable manner. Potential cross-interference with operating room electronic instrumentation is minimized by shielding. System cost and space requirements are substantially lowered. An accidentally retained surgical implement is discovered in a timely manner, prior to completion of surgery and before the patient has been removed from the operating room. The portable detection unit is adapted to be transported to a second location from which the potential cross-interference between the electrical or magnetic fields generated during operation of the detector and the electronics deployed during the surgery is minimized. The patient is interrogated after closure of the wound by being subjected to an interrogating field generated by the surgical implement detector at the second location. Visible and/or audible signals from the detector signify accidental retention of a surgical implement before the patient awakes.

6 Claims, 6 Drawing Sheets

PORTABLE SURGICAL IMPLEMENT DETECTOR

BACKGROUND OF THE INVENTION

1. Field of the Invention

The present invention relates to a system for detection of surgical implements; and more particularly, to a method and means for detecting a marked surgical implement such as a sponge, scissors, clamp, or other instrument within a surgical wound in human or animal tissue.

2. Description of the Prior Art

During the course of a surgical operation it is generally necessary for a variety of articles, such as surgical sponges, gauzes, instruments and the like, to be placed into a wound cavity. Despite rigorous precautions designed to retrieve these items and ensure their removal prior to completion of the surgical procedure and closure of the surgical incision, such items are sometimes inadvertently lost during surgery and remain within the patient. When this occurs, serious consequences often ensue. The patient may suffer pain, infection, intestinal obstruction, and even death. An additional invasive surgical procedure is then necessary to remove the foreign object in order to prevent serious, and possibly fatal, consequences to the patient. The problem of retained surgical implements has been recognized since the earliest days of surgery. The procedures traditionally employed to prevent post-surgical implement retention include manual search of the wound by the surgeon prior to closure and a careful accounting for all materials inserted and removed from the wound. This accounting function is customarily carried out by the operating room staff, usually the circulating nurse. Notwithstanding these precautionary measures the accidental retention of surgical implements continues to occur to this day with disturbing regularity, even in highly respected institutions. Surgeons and related medical professionals regard this unfortunate mishap as a major unsolved problem.

At present, physical count combined with manual search remain the primary procedure used for detecting retained surgical implements. Nevertheless, the above-mentioned failures of the conventional procedures have led to other approaches, such as the use of x-ray methods. Most surgical instruments are composed of metal, and are easily visible on x-ray. Sponges are generally made to bear a radiopaque component to make them also visible on x-ray. However, intraoperative x-rays are not routinely performed before closure of the incision for several reasons: They entail the risk of extension of operative time and anesthesia, along with undesirable expense, inconvenience, and radiation exposure. Postoperative x-rays are subject to some of the same disadvantages and are not generally done unless there is a specific question of a retained implement in a given case. Moreover, even when postoperative x-rays are obtained, retained surgical implements are still overlooked in many cases, owing to the presence of other competing shadows on the film. If a retained article is detected, a timely second operation is required to effect its removal, notwithstanding the further trauma to the patient. The severity of the problem clearly warrants efforts that allow the aforementioned consequences to be avoided altogether by ensuring removal of the offending articles before surgery is completed, not at a later point.

Over the years many efforts have been made to prevent the accidental retention of surgical implements. It has been suggested that the implements be provided with a radioactive tracer. This technique, disclosed by U.S. Pat. No. 2,740,405 to Riordan, is subject to obvious hazards associated with use, storage and disposal of radioactive materials and has never gained general acceptance It has also been proposed that surgical sponges be marked with a flexible plastic impregnated with either paramagnetic or ferromagnetic materials in the form of powders. Detection of these marked sponges is accomplished by a metal detector. This method, taught by U.S. Pat. No. 3,422,816 to Robinson et al., provides very small signals difficult to detect over the width of a patient's body. In addition, the Robinson et al. technique provides no discrimination against other metal objects, such as a stent or staple which, though present within the surgical wound, are appointed for retention therewithin.

Yet another proposal, advanced by U.S. Pat. No. 3,587,583 to Greenberg, involves use of surgical sponges marked with magnetized particles whose presence is detectable with magnetodiodes. In practice, however, the magnetic field generated by these particles is too small to be readily detected by the diodes.

U.S. Pat. No. 4,114,601 to Ables discloses the use of a small transponder fixed to a surgical sponge or instrument. This transponder exhibits gyromagnetic resonance at preselected frequencies. Detection is accomplished by nonlinear mixing of two frequencies impinging upon the transponder. The gyromagnetic resonance effect disclosed by Ables is a high-frequency phenomenon, existing at frequencies of the order of about 5 gigahertz (5,000,000,000 cycles/sec). These frequencies, known as microwaves, are absorbed readily by tissue. In use of the Ables-type transponder, the energy developed goes primarily into heating tissue, rather than exciting the transponder into gyromagnetic resonance.

U.S. Pat. No. 4,510,489 to Anderson et al. discloses an article surveillance system especially useful in the protection of articles from theft from retail businesses and similar institutions. The system employs a magnetomechanically resonant marker and detection electronics for sensing the presence of the marker.

U.S. Pat. Nos. 5,057,095, 5,107,862, 5,190,059, 5,329,944, 5,105,829, and 5,188,126 to Fabian et al. disclose the use of various technologies to detect surgical implements marked with a tag and left within the surgical wound after completion of surgery and prior to closing the wound. In these patents, the detection apparatus is utilized in the operating room, since detection is accomplished before closure of the wound. While these systems are effective in detecting marked surgical implements, the electromagnetic fields generated during operation of the systems may interfere with other medical electronics, such as heart monitors, extant in the operating room. Since such devices require operating room personnel to diligently scan each patient, the potential for operator error is always present. The units had two components, one of which was designed to be intrinsic to the operating table itself. Therefore, to assure reliable detection of surgical implements during an operation, a separate unit is required in each operating room, entailing high cost and space requirements.

Thus, up to the present time, the optimal means for detecting post-operatively retained surgical implements, though addressed by numerous workers in the art, have yet to be found. Instead, the detection systems heretofore proposed each have significant drawbacks allowing for correction.

SUMMARY OF THE INVENTION

The present invention provides a portable detection system and method for detecting surgical implements within human tissue in an accurate, reliable manner. System cost and space requirements are significantly reduced and retained articles are detected and accurately localized prior to wound closure. A secondary detection procedure conducted outside the operating room but inside the operating room suite and within close temporal proximity of the operation increases detection efficiencies without disrupting electronics deployed during surgery.

Generally stated, the invention provides an improved system for detecting in human tissue a surgical implement used during a procedure carried out in an operating room. A marker attached to the surgical implement changes its impedance at a preselected frequency in the presence of an electromagnetic field. The change of impedance provides the marker with signal-identifying characteristics. In accordance with the improvement, the entire detection system is packaged for portability. A surgical implement with its attached marker is deployed within the wound during the operation and if said surgical implement and attached marker are inadvertently retained within the wound, the signal-identifying characteristics are detected while the patient is still on the operating table. The detection system is readily transported to a locus within the operating room suite for further use shortly after the operation to assure accurate detection of retained surgical implements without disrupting electronic instrumentation attending the surgery. The ease of use of the present portable system allows the patient to be scanned very quickly, so that retained implements can be located and removed even prior to closure of the wound. By way of contrast, if an implement is detected by a prior art system used postoperatively, the patient must be re-anesthetized and the wound re-opened and re-closed to remove the offending item.

Specifically, the invention provides a portable detection system wherein an interrogating means generates an electromagnetic field having a preselected interrogating frequency modulated as a series of pulses, the marker attached to the surgical implement resonates at a preselected frequency in response to the field, and a detecting means detects a ring-down signal of the marker between the pulses. It will be understood that the interrogating frequency used in the practice of various embodiments of the present invention may be a range of frequencies. That is to say, the interrogating frequency may be chirped, or swept through a preselected range encompassing the resonant frequency of the tag, to ensure that the resonance is excited. In some implementations the sweep range encompasses more than one frequency band, whereby markers having different nominal resonant frequencies may all be detected. For example, magnetomechanically resonant tags resonant at different frequencies generally have different lengths. A system wherein the interrogating frequency is swept through multiple frequency ranges may be used to detect tags of different sizes selected as being appropriate for the variety of different surgical items needed to carry out requisite medical tasks.

The marker comprises a magnetomechanical element having a mechanical resonance frequency substantially equal to the preselected frequency, and a biasing means for magnetically biasing the magnetomechanical element. A housing is provided for enclosing the magnetomechanical element and the bias means, wherein the magnetomechanical element is free to mechanically vibrate.

Alternatively, the marker is comprised of an electrically resonant LRC circuit, or as a further alternative, the marker is comprised of a mechanically resonant piezoelectric material and coils.

Further, the invention provides a method for detecting a retained surgical implement by affixing a marker to a surgical implement appointed for use during an operating procedure, bringing a portable surgical implement detector to the patient's bedside to detect the implement if inadvertently the implement is not removed from the patient in a timely manner. Preferably, the portable detection unit contains its own intrinsic shielding to minimize the possibility of interference with electronic equipment present in the environment. Detection of the marker is indicated visually and/or audibly by the detector. Moreover, the portable detection unit is readily transported to a location outside the operating room, such as a location generally within the operating room suite, and optionally used there shortly after surgery to assure the detection of retained surgical implements without application of magnetic fields in the vicinity of operating-room instrumentation.

Advantageously, the method and apparatus of the invention detect retention of surgical implements with far greater accuracy than with conventional methods and means involving a physical count of implements that enter and exit the wound. The apparatus is inexpensive to construct, safer for the patient than postoperative X-rays and avoids risk to the patient and the environment posed by radioactive tracers. The signal generated by surgical implements items tagged with the marker of the invention renders them far more readily detectable than items such as sponges bearing magnetized particles whose magnetic field is to be sensed. Moreover, the present system operates without the heating of tissue caused by microwave detection systems. Detection of implements marked in accordance with the invention is accomplished irrespective of marker position or orientation within the wound. Possible electrical interference with operating-room instrumentation is minimized and space requirements and system costs are substantially reduced, since one system can service multiple rooms.

The portability of some embodiments of the detection system of the present invention conveys a number of advantages. Systems having antenna and receiver elements that are positionable in a variety of orientations with respect to the patient being scanned are especially beneficial. Many known markers have greater sensitivity to incident electromagnetic fields having a preferential orientation or range or orientations. Since the orientation of a marker borne on a retained implement is unknown and generally random with respect to the patient's body, the ability to scan with interrogating fields in different orientations markedly enhances the likelihood that a given marker will not go undetected. The positionable orientation of both incident field and detecting coils is inherent in many implementations of the present portable system, including those with the transmitting and/or receiving elements disposed either in paddles, wands, or movable housing components. As used herein, the term paddle includes any hand-held and maneuverable structure comprising at least one transmitting or receiving element of the portable detector system. The paddle may further comprise multiple transmitting or receiving elements or the like. All or part of the electronics of the system and the power sources, including batteries, may be contained in the paddle. Alternatively, the paddle and any circuitry present therein may be connected to other portions of the detection system by wire, fiber optic link, or wireless communication for power or signal transmission.

By way of contrast, previous systems having permanently mounted elements generally lack the extent of flexibility of the present system, inasmuch as it is generally impractical to manipulate the patient's position to change his/her orientation to any great extent relative to the system's elements.

Some implementations of the present portable system are operable in venues wherein prior art systems are impractical or impossible to use. For example, the increasingly sophisticated nature of medical and surgical technology frequently has caused operating rooms to become crowded with devices and instrumentation deemed essential for the expected level of ordinary care. The portability of the present system allows it to be brought to its point of use at the time of need, without occupying limited operating room space or impeding the operating room staff at other times.

The versatility of the system also makes it highly useful in transportable and mobile medical and surgical treatment facilities, such as field hospitals, that are often deployed by military forces in remote locations for treating battlefield injuries. The physical and operational conditions under which military personnel and other patients are surgically treated in such facilities are often far from optimal, making it even more likely in some instances for surgical items to be overlooked. A portable system of the invention may be readily and advantageously used in this environment. Its functionality is enhanced by use of rechargeable battery power and the ease of situating it proximate the surgical location. Implementations wherein the detection electronics and optionally a battery power source are housed in a back-pack further enhance the functionality of the system for use in such facilities.

BRIEF DESCRIPTION OF THE DRAWINGS

The invention will be more fully understood and further advantages will become apparent when reference is had to the following detailed description of the preferred embodiment of the invention and the accompanying drawings, in which.

DESCRIPTION OF THE PREFERRED EMBODIMENTS

Figure 1:
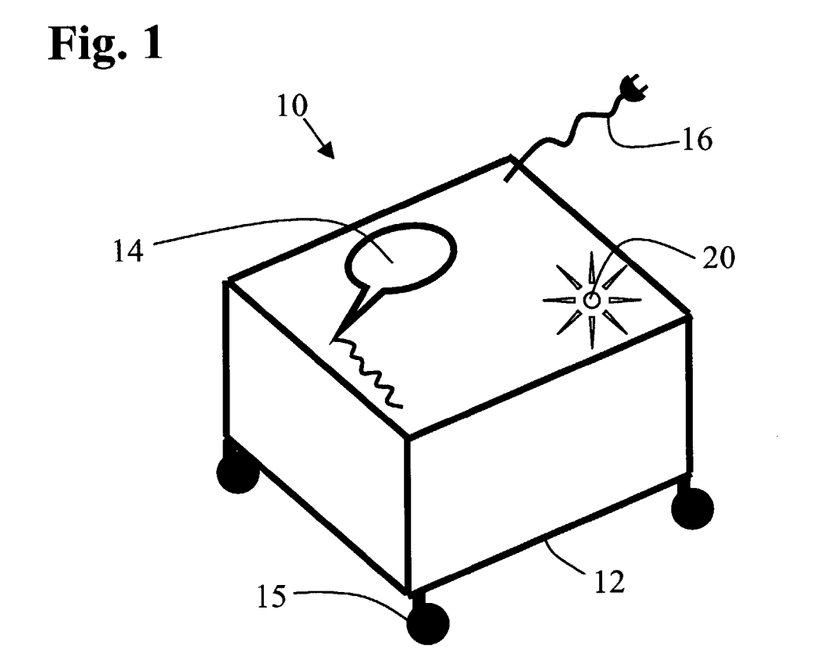
FIG. 1 is a perspective view illustrating a portable surgical implement detection unit of the present invention.

Referring to the drawings, there is shown generally at 10 in FIG. 1 a freely movable, portable device for detection of surgical implements. The portable detection device 10 comprises detection electronics (described hereinafter) contained within housing 12. A scanning paddle 14 comprising an antenna means of the device is adapted to rest on housing 12. The housing is provided with casters 15, skids (not shown), or the like, for facilitating movement thereof. Plug 16, electrically connected to the housing electronics, is adapted for connection to a power supply, such as an electrical outlet, or the like. Preferably, the housing has an audible or visible alarm means, such as light 20, which rings, blinks or otherwise signals the user when a retained surgical implement is detected, allowing timely intervention and removal of the offending object, and averting untoward medical consequences for the patient.

Figure 2:
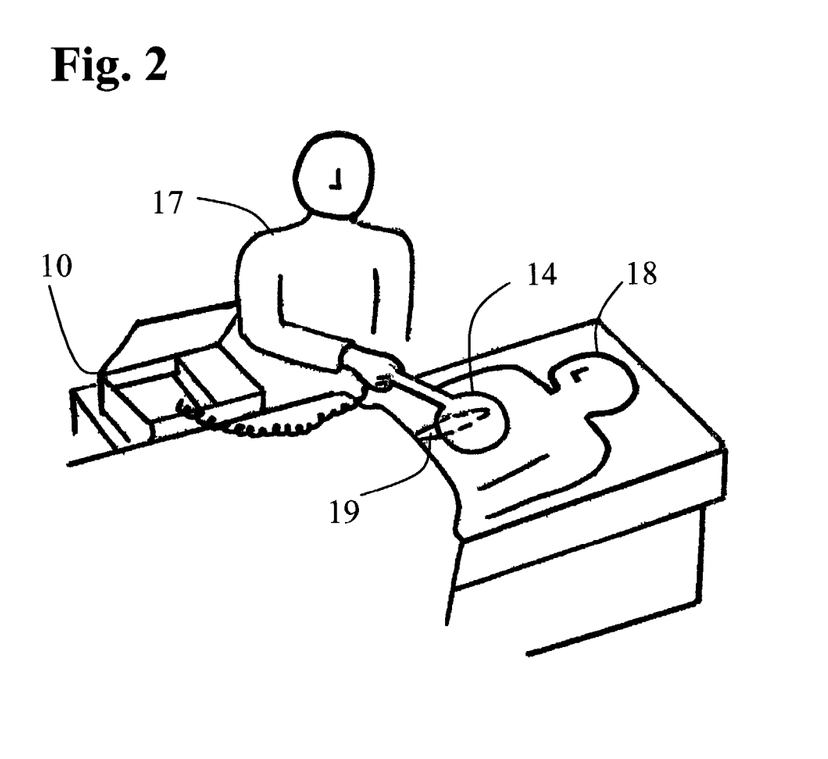
FIG. 2 is a perspective view that depicts a patient's incision being scanned with a handheld detection unit of the invention by a trained operator.

Referring to FIG. 2 of the drawings there is shown an operator 17 scanning an incision 19 in a patient 18 with a handheld detection device, such as scanning paddle 14 of portable detection unit 10. Markers appointed for use with unit 10 can exhibit three types of resonance in the presence of an applied magnetic field: (1) magnetomechanical—in which case energy is alternatively stored in mechanical vibration and magnetic field, such as can be seen with a magnetostrictive amorphous ribbon; (2) electromechanical—in which case energy is alternately stored in mechanical vibration and electric field, such as can be seen with a piezoelectric crystal; and (3) electromagnetic—in which case energy is alternately stored in an inductor and a capacitor, such as can be seen with an LRC circuit. When excited by interrogating means (such as means 113 shown in FIG. 8), each marker will generate a dipole field that exhibits a characteristic phase difference with the exciting field near resonance and a shift in phase as the exciting field's frequency traverses resonance. Since energy from the exciting field is being stored in these resonant elements, removal of this field will result in the gradual loss of the energy from the element, yielding a dipole field having a characteristic "ring-down" of energy and providing the marker with a signal-identifying characteristic.

Figure 3:
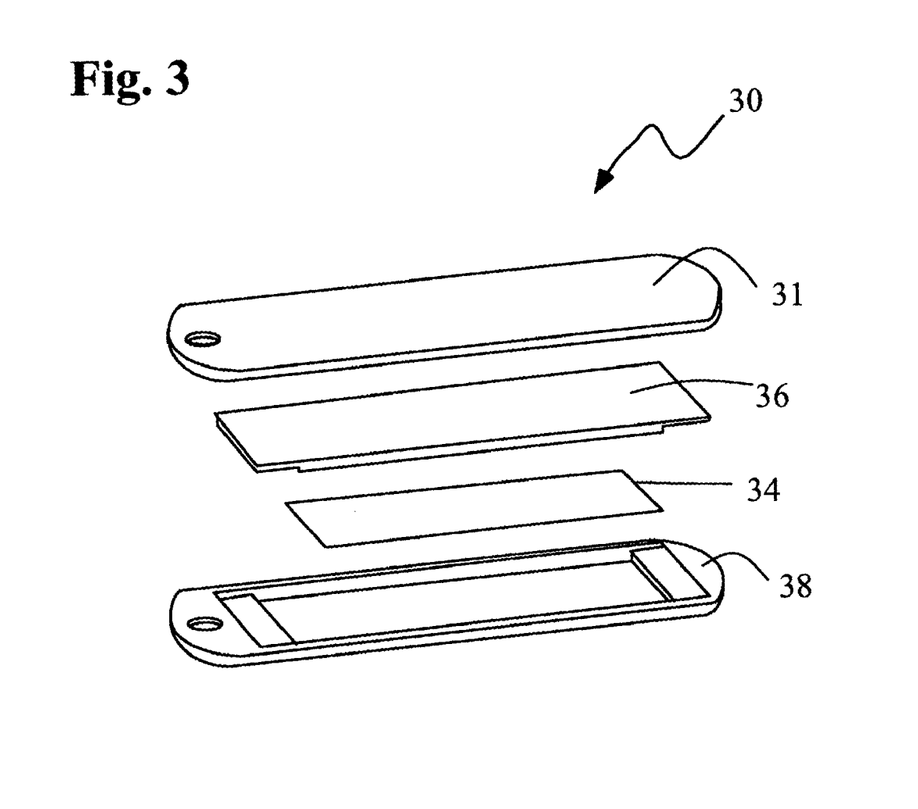
FIG. 3 is an exploded, perspective view illustrating a magnetomechanical marker useful in the practice of the present invention.

FIG. 3 is an exploded view of the preferred embodiment for the marker. Magnetomechanical marker 30 comprises a strip of magnetostrictive material 34 adapted to be magnetically biased and thereby armed to resonate mechanically at a preselected frequency within the frequency band of the interrogation field. A semi-hard or hard ferromagnetic element 36 disposed adjacent to the strip 34 of magnetostrictive material is adapted, upon being magnetized, to arm the strip 34 to resonate at the preselected frequency. Preferably, biasing magnetic material of either type has a magnetic coercivity sufficient to prevent the material from becoming demagnetized due to inadvertent exposure to other magnetic fields. Case 38 and lid 31 comprise a material, such as ABS plastic, that will remain inert within the wound throughout the surgery. The strip 34 of magnetostrictive material has a magnetomechanical coupling factor greater than zero. The hard ferromagnetic element 36 is preferably a molded composite composed of a hard ferromagnetic powder, such as barium ferrite, and a plastic such as nylon or delrin. The concentration of magnetic powder to plastic is selected to supply a field substantially equal to the magnetic field required to obtain optimum magnetomechanical coupling in the magnetostrictive strip 34. For example, approximately 3 Oersteads of magnetic bias is required to obtain maximum magnetomechanical coupling in an unannealed amorphous alloy whose composition is substantially equal to 40% Fe, 38% Ni, 4% Mo, and 18% B, percentages in atomic percent. Alternatively, hard ferromagnetic element 36 is a thin strip of metal alloy such as vicalloy or Arnochrome. Upon exposure to the DC magnetic field, generated by the hard ferromagnet 36, or generated externally, the marker is characterized by a substantial change in its effective impedance as it undergoes resonance when the preselected frequency is supplied by the interrogating field. When the interrogating field is removed, the magnetostrictive strip 34 exhibits the characteristic ring-down at the resonant frequency. The preselected frequency is chosen to be substantially equal to the mechanical resonant frequency of the magnetostrictive strip or a harmonic thereof.

A variety of magnetostrictive amorphous metal alloy ribbons are useful in the construction of the magnetomechanically resonant marker of the present invention. Many amorphous metals combine high mechanical hardness and relatively low magnetic anisotropy and loss, leading to low internal friction, a high magnetomechanical coupling factor and magnetomechanical resonance with high Q. One amorphous metal suitable for the present marker consists essentially of the aforesaid alloy having 40% Fe, 38% Ni, 4% Mo, and 18% B (atomic percentages) plus incidental impurities. Other amorphous metal alloys exhibiting desirable magnetomechanical behavior are also useful in the present marker.

Figure 4:
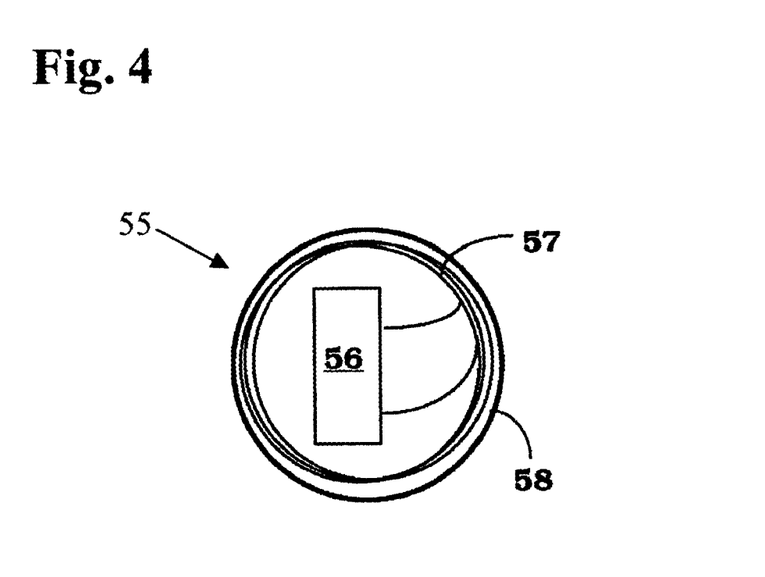
FIG. 4 is a perspective view illustrating the main elements of an electromechanical marker useful in the practice of the present invention.

An alternative embodiment of the marker is shown in FIG. 4. In the embodiment shown, the marker 55 comprises a piezoelectric element 56. The piezoelectric element comprises a piezoelectric material, such as a quartz crystal, PZT, or a piezoelectric film, such as Kynar film. The piezoelectric element is provided with terminals for electrically connecting the element to other circuit elements such as a coil. An air-core coil 57, occupying the inside diameter of case 58, is terminated across piezoelectric element 56 and is inductively coupled to the interrogating field of the detection system. Alternatively, an iron or ferrite core inductor is used in place of the coil 57. The marker 55 is characterized by a substantial change in its effective impedance at the resonant frequency which provides the marker with signal identity. When the field is removed, the marker exhibits ring-down at the resonant frequency. The preselected frequency is chosen to be substantially equal to the mechanical resonant frequency of the piezoelectric material or a harmonic thereof.

Figure 5:
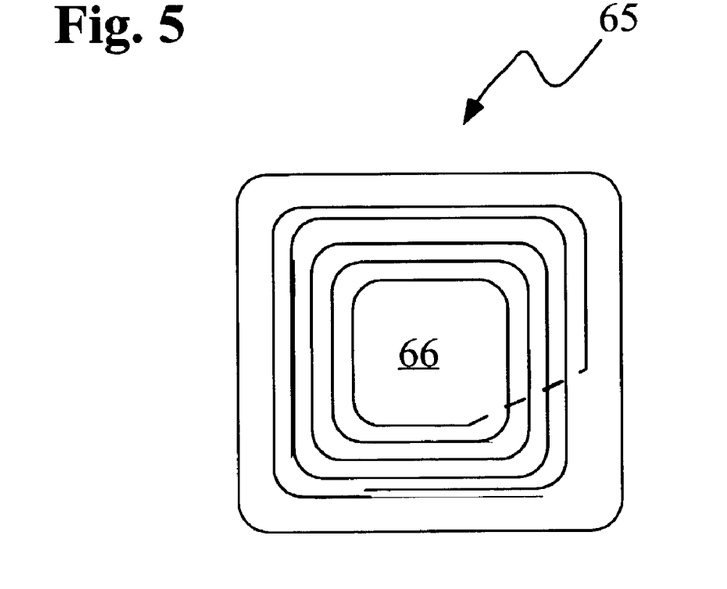
FIG. 5 is a plan view depicting the main elements of an electromagnetic marker.

A further embodiment of the marker is shown in FIG. 5. In that embodiment, marker 65 comprises a printed circuit coil 66. The resonance frequency of coil 66 is determined by the inductance, capacitance and resistance of the coil. Alternatively, marker 65 comprises an inductor, resistor, and capacitor in a series or parallel LRC circuit. Such a marker is rendered small with the use of surface mounted components. The marker is characterized by a substantial change in its effective impedance at the resonant frequency, thus providing marker 65 with signal identity. This signal identity is characterized by phase change and electrical ring-down at the resonant frequency when the applied field is removed. The preselected frequency is chosen to be substantially equal to the electrical resonant frequency of the LRC circuit or a harmonic thereof.

Figure 6:
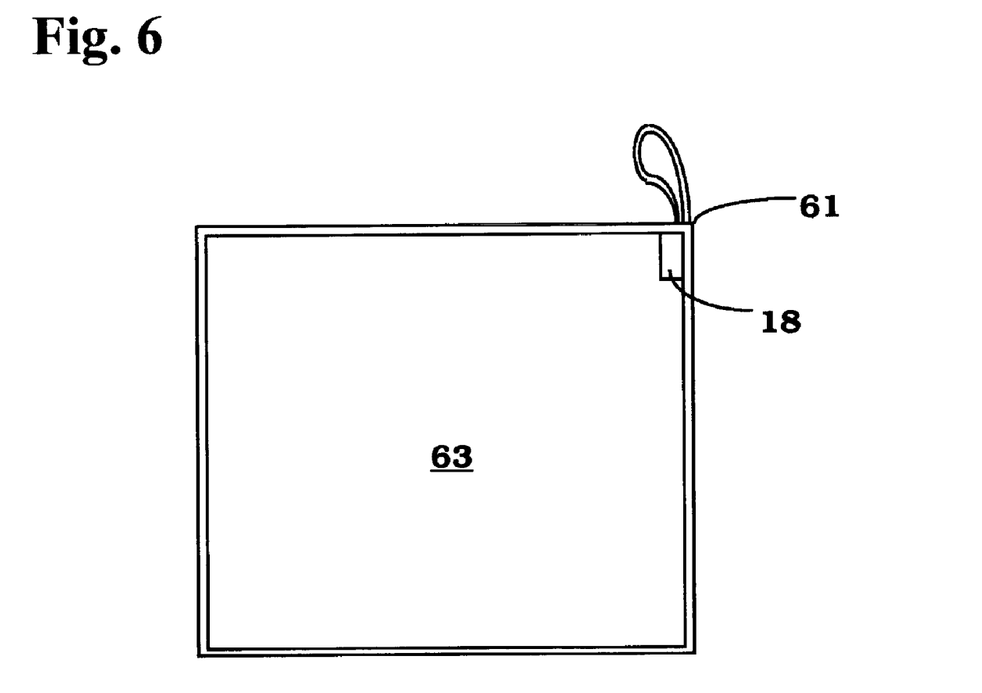
FIG. 6 is a frontal view depicting a surgical sponge with a marker sewn into a corner.
Figure 7:
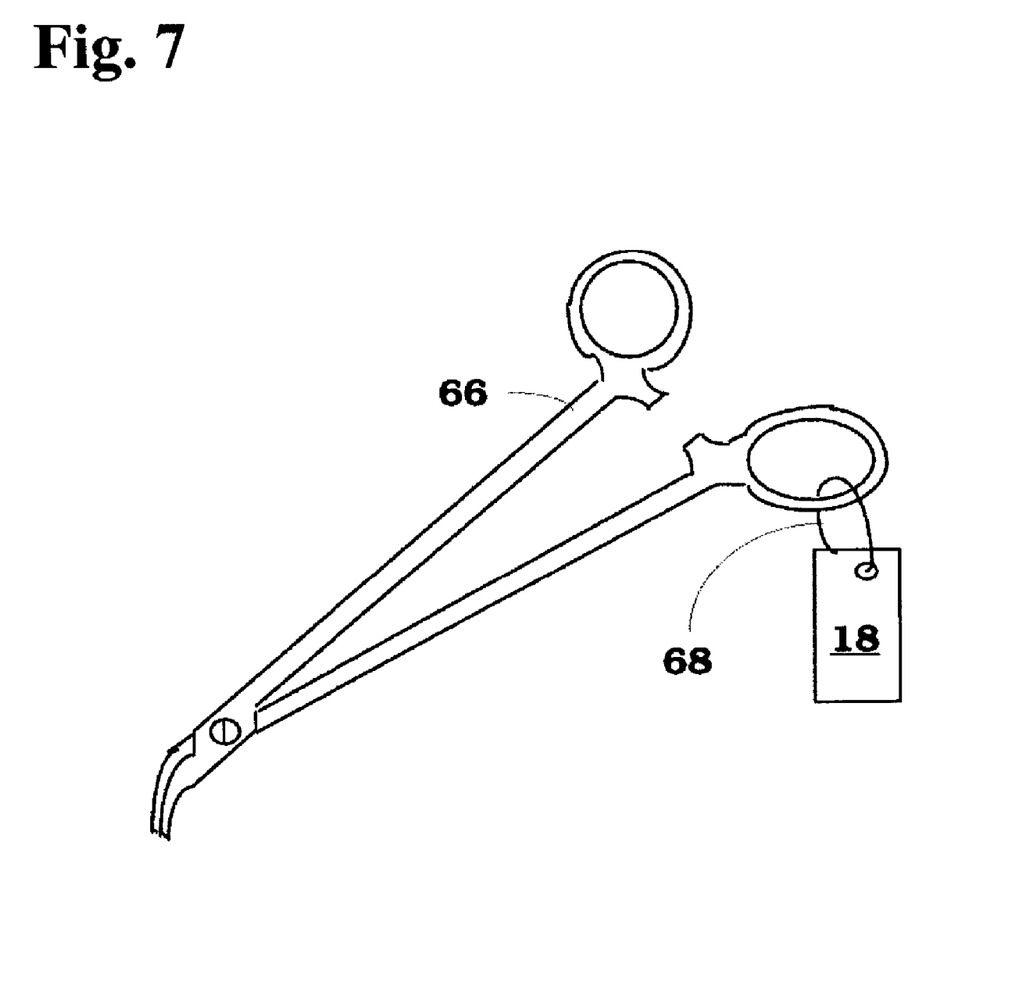
FIG. 7 is a perspective view depicting a surgical forceps having a marker attached thereto by a lanyard.

The marker can be attached to various surgical implements. As shown in FIG. 6, marker 18 is sewn into a corner 61 of a surgical sponge 63. FIG. 7 shows marker 18 attached to forceps 66 by lanyard 68. Alternatively, marker is fixed to forceps 66 by adhesive.

Figure 8:
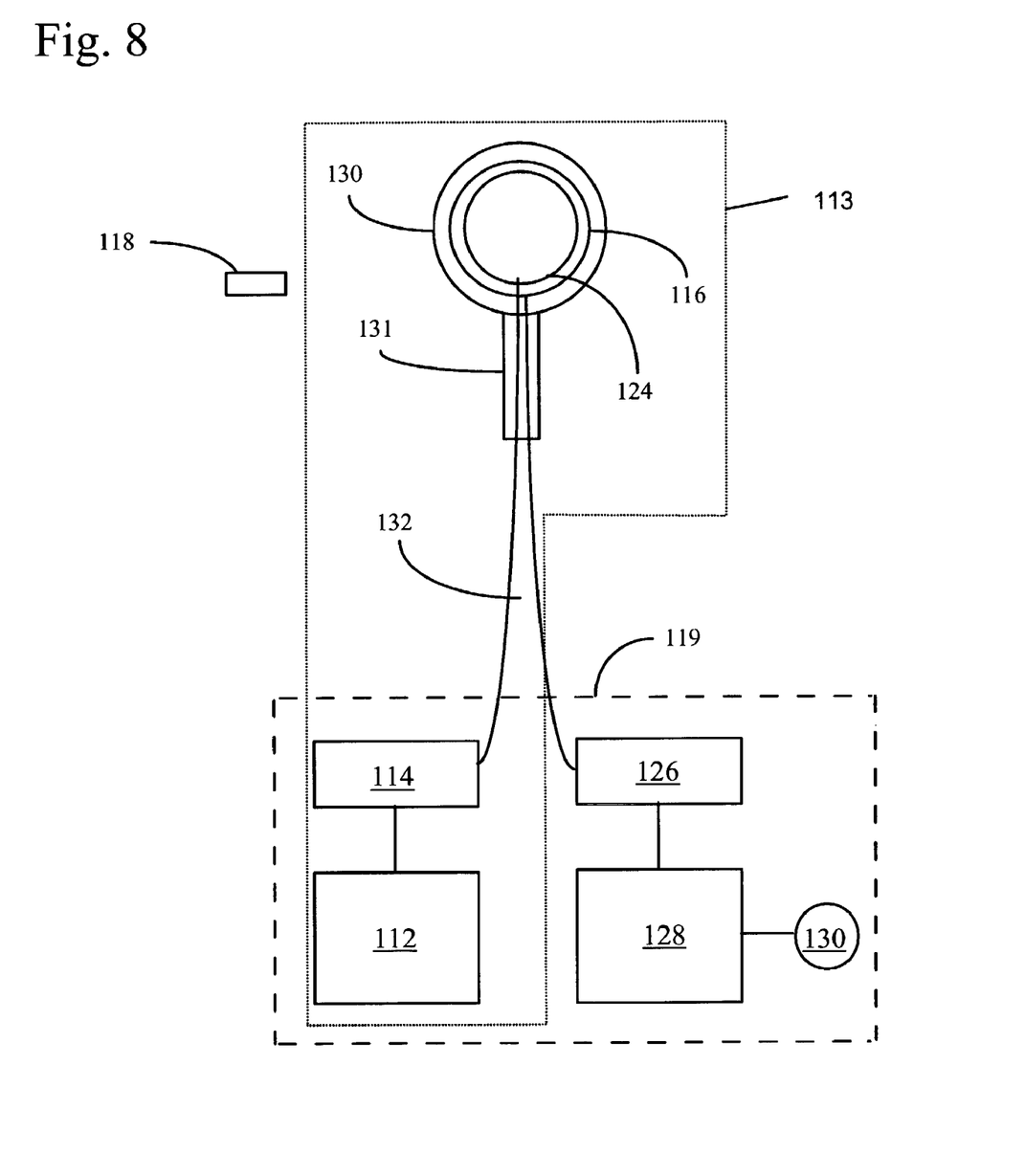
FIG. 8 is a diagrammatic representation of a portable surgical implement detector having a field-changing means, frequency-generating means, antenna changing means, detecting means, and indicator, as main elements thereof.

Preferably, as shown in FIG. 8, paddle 130 has handle 131 comprising field-generating means 116 and detecting antenna 124. Electrical leads 132 connect paddle 130 to portable surgical implement detector 119. Portable surgical implement detector 119 comprises field-changing means 114, frequency-generating means 112, antenna changing means 126, detecting means 128, and indicator 130.

Marker 118 is attached to a surgical implement appointed for use within the wound of a patient. Interrogation means 113, used to interrogate the patient for the presence of marker 118, comprises frequency-generating means 112, field-generating means 116, and field-changing means 114. Frequency-generating means 112 supplies a power signal from an AC power source to the field-generating means 116. It generates a frequency encompassing the resonant frequency of the marker, thereby exciting the marker into resonance. A field-changing means 114 varies the amplitude and direction of the magnetic field to alter the electromagnetic dipole coupling between the marker 118 and the magnetic field provided by the field-generating means 116. Detecting antenna 124 receives the varying magnetic field caused by the resonating marker. A detecting means 128 detects the signal received by detecting antenna 124. Detecting means 128 detects the resonant frequency of the marker and its associated signal-identifying characteristic. Below 10 MHz, generating means 116 and detecting antenna 24 are both typically comprised of one or more coils. Above 10 MHz, generating means 116 and detecting antenna 124 are both typically comprised of one or more monopole antennas or, alternatively, dipole antennas.

The signal detected at detecting antenna 124 by the aforesaid marker 118 is a product of the efficiency of energy transfer or coupling between the generating antenna 112 and the marker 118, and the efficiency of energy transfer or coupling between marker 118 and detecting antenna 124. Upon detection of marker 118, detecting means 128 causes indicator 130 to alarm by sounding a buzzer and/or flashing a light. In practice, the portable surgical implement detector is brought to the patient during or after surgery and the paddle is moved in the vicinity of the wound.

Alternatively, two paddles each of which has a field-generating means and a detecting means are connected in parallel to the portable surgical implement detector, further enhancing the detection of markers. The paddles are placed on opposite sides of the wound to detect for the presence of markers.

As a further alternative, two paddles are used, but a first paddle houses detecting means 124 and a second paddle houses field-generating means 116. With this configuration, the two paddles are placed on opposites sides of the wound.

The portable surgical implement detector described herein can receive power from an AC power source in the conventional way. Alternatively, the portable surgical implement detector is battery powered, receiving DC power from a battery (not shown), which is preferably rechargeable. This embodiment so improves portability of the surgical implement detector, that it is ideally suited for use in field operations where surgical procedures and recovery stations are located in separate tents, barracks or the like. In addition, potential shock hazards, line-conducted electromagnetic interference with other electronic equipment, and ground-loop interferenceare also eliminated in battery-powered embodiments that are not connected to any AC power source during use.

Figure 9:
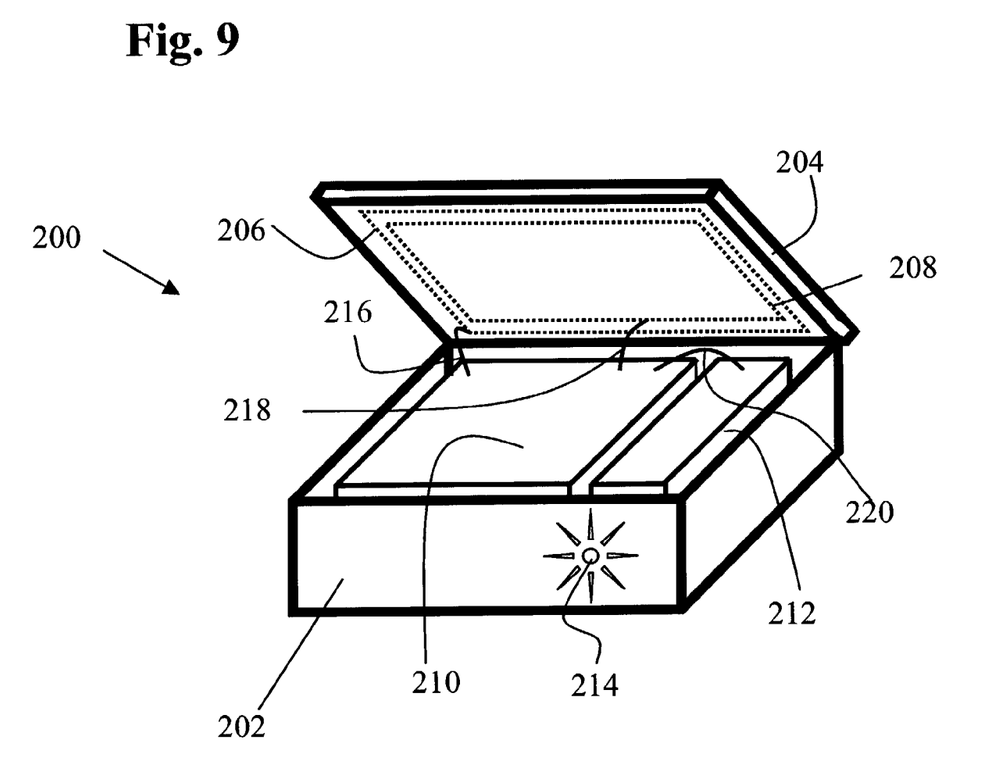
FIG. 9 is a perspective view of a portable surgical implement detector of the invention which is housed in a portable case with a hinged lid in which are mounted transmitter and receiver coils.

In another embodiment of the present invention depicted by FIG. 9, the detection system 200 is housed in a case 202 which is similar to a briefcase or suitcase and has a hinged, openable lid 204. Advantageously, transmitting coil 206 and receiving coil 208 are affixed generally concentrically to lid 204, whereby the orientation of the coils is changed upon the customary motion of the lid as it is reversibly moved between its open and closed positions and positions intermediate thereto. In an alternative embodiment, receiving coil 208 takes on a figure-eight configuration instead of the generally rectangular shape depicted. The change in coil orientation effected by lid motion, in turn, changes both the orientation of the interrogating electromagnetic field produced by transmitting coil 206 and the coupling of the dipole field emitted by an activated marker of the invention into receiving coil 208. System 200 further comprises detection electronics 210 and a battery 212 housed in case 202. Battery 212 is preferably rechargeable by connection to the electrical mains or a battery charger of conventional design (not shown). As discussed above in greater detail, favorable orientation of the transmitting and receiving coils 206, 208 with respect to the marker enhances the probability that the marker will be suitably excited and detected. Optionally, the embodiment depicted by FIG. 9 further comprises additional transmitter or receiver coils. One or more of these coils may be contained in a paddle similar to paddle 130 depicted by FIG. 8 or they may be deployed on arms that telescope or fold out from a storage position into an operating position. In this and other embodiments of the invention, at least one of the transmitting and receiving coils my be moved by motion means that may comprise any combination of mechanical, electrical, and pneumatic elements that may be under automatic control or activated manually by an operator. Transmitter coil 206 and receiver coil 208 are connected to electronics 210 by cables 216 and 218, respectively. Battery 212 powers detection electronics 210 via cable 220. Upon detection of a marker emitting a marker dipole field carrying the requisite signal-identifying characteristic, detection electronics 21 activates strobe light 214 to alert the attending medical personnel.

The orientation sensitivity of markers generally has not posed a problem in use of article surveillance systems employed for purposes of antitheft, access control or sorting. In these systems, the marker is attached to an article or person moving through the interrogation zone, and is thereby caused to move into strong signal zones. The interrogating field orientation generally varies in direction within the interrogation zone, so it is highly unlikely for a marker to traverse the zone without becoming sufficiently favorably oriented at some point to allow detection in the normal manner. However, the extent of motion of a marker affixed to a surgical implement embedded within a surgical wound is far smaller. Practical limitations on the manipulation of a patient during and after surgery make it highly desirable that the detection method comprise motion of the antenna and receiver element. For the reasons set forth previously, the necessity for achieving the highest degree of accuracy in detection of retained surgical implements is readily apparent. Moreover, patients vary greatly in size, so that small antenna structures such as paddles are well adapted to be manipulated into optimal position for detection. Certain medical situations, such as an obese patient, make it further desirable to have the flexibility afforded by movable antenna structures.

Many of the embodiments of the detection system of the invention preferably employ a plurality of antenna elements, detection elements, or both. The elements may be disposed either in a fixed mutual arrangement or in a plurality of subsidiary structures (such as paddles 130 depicted by FIG. 8) allowing relative motion of the elements. If multiple antenna or detection elements are present, they may be connected in a fixed circuit arrangement, such as in series. Preferably, a switching system is employed to activate them switchably in different circuit configurations in which any number of the elements are operated singly or in combination. Different connections may be established sequentially during the operation of the system, either under automatic control of the switching system or in response to manual activation by the operator. The switching system may be of any type, but preferably is electrical or electro-mechanical; more preferably, it employs semiconductor switching elements. The polarity of a series connection of antenna elements established by the switching system may also be inverted, thereby changing by a half cycle the relative phase of the time-varying field produced by each coil. Each combination of a pair of transmitting coils and a relative polarity gives rise to an interrogating field within the interrogation zone that has a different spatial distribution and vectorial orientation. A marker generally is found to be most sensitive to excitation by an interrogating field having a strong vector component along a particular preferred marker orientation. As a result, sequential excitation of the target by differently oriented interrogating fields markedly increases the probability that a given marker will be favorably oriented within at least one of such field patterns, thus markedly decreasing the probability that a marker will pass through the interrogation zone without being activated by the interrogating field and consequently detected. In a system having but a single fixed antenna element, there is a slight probability that a marker in an orientation that is fortuitously unfavorable might escape detection.

The same considerations of magnetic superposition and reciprocity that make preferable the use of a field-generating means comprising a plurality of antenna elements also apply to the detecting antenna of the present system, which preferably comprises a plurality of receiver elements. In addition, it is likewise preferable that the receiving means comprise an electrical, electromechanical, or semi-conductor-based receiving switching system by which one or more receiver elements are selectively connected to the detecting means. The strength of the signal received from the dipolar field emanating from the marker is enhanced by proximity of the marker to the receiver elements and favorable relative orientation of the marker and the one or more active receiver elements. It is further preferred that plural receiver elements be coupled to enhance the sensitivity and coverage of the detector. Like the interrogating field, the oscillating electromagnetic field produced by the marker during its ring-down period has a spatial distribution and vectorial orientation. Connecting the output of the antenna system in sequentially varied different configurations to the detection system enhances the sensitivity of the system to signals and the probability of detection.

The combination of varying the orientation of the detector and interrogation field is especially beneficial in detecting markers that produce a weak output. Enhanced detection sensitivity advantageously allows use of markers having reduced amounts of magnetic material and reduced size that otherwise could not reliably be detected.

In still another embodiment of the invention, the marker comprises a memory element wherein a predetermined code is stored. The marker is operative in the presence of the interrogating field to transmit the predetermined code. The detecting means used in this embodiment receives the transmitted code and activates indication means if the received code is that of a marked surgical instrument. Advantageously, certain embodiments employing such coded markers may be used for further identification purposes, such as distinguishing between various types of instruments or even of identifying specific instruments.

Advantageously, with use of the portable surgical implement detector, instrumentation is minimized. Only one detector is needed per operating room complex, minimizing cost and floor space. To prevent the retention of surgical implements inadvertently left in the body after surgery, a marker is attached to each surgical implement appointed for use within the surgical wound. Prior to the wound being sutured and closed, a portable surgical implement detector is brought to the patient's side. The patient is subjected to the interrogation field generated by the surgical implement detector, which provides a visual and/or audible signal if the marker is present.

More specifically, to prevent a surgical implement inadvertently left in a surgical wound of a patient, a marker is attached to each surgical implement appointed for use during an operating procedure. A surgical implement detector is brought to the patient before the operation is completed and the wound is closed. The marker comprises a marker element adapted to undergo resonance at a preselected frequency generated by the surgical implement detector. Following the surgical procedure, the patient is subjected to an interrogation field generated by the surgical implement detector. A visual or audible alarm triggered by the detector indicates the presence of a marker within the interrogation zone.

Preferably, to reduce possible interference with operating-room instrumentation, the housing containing the surgical implement detector is lined with shielding. When the preselected frequency is below 10 MHz, the shielding preferably comprises a low permeability magnetic material, low coercive field material, such as permalloy, mumetal, or the like. Above 10 MHz, the shielding is comprised of a grounded metal screen.

To further minimize cross-interference with operating-room instrumentation, the portable implement detector is transported to a nearby location that is sufficiently remote from the operating-room instrumentation that such interference is substantially eliminated. Such a location can include a common hallway outside the operating room but within the operating room suite. Shortly following closure of the wound, the patent is again interrogated by the portable implement detector at the aforesaid remote location. This procedure maximizes detection accuracy and virtually eliminates cross-interference with operating-room instrumentation.

Having thus described the invention in rather full detail, it will be understood that such detail need not be strictly adhered to but that various changes and modifications may suggest themselves to one skilled in the art, all falling within the scope of the invention as defined by the subjoined claims.

We claim:

1. In a system for detecting in human or animal tissue a surgical implement used during an operating procedure carried out in an operating room wherein a marker attached to said surgical implement changes its impedance at a preselected interrogating frequency in the presence of an electromagnetic interrogating field which provides said marker with signal-identifying characteristics, the improvement wherein:

said marker comprises at least one marker element adapted to undergo resonance at a preselected resonant frequency and radiate a marker dipole field in response to said interrogating field; said signal-identifying characteristic is a ring-down of said dipole field; the surgical implement is deployed within the wound during the operating procedure; and said signal-identifying characteristics are detected by a freely movable, portable detection unit comprising:

an interrogating means that comprises a frequency-generating means for generating said preselected interrogating frequency, a field-generating means for receiving said preselected interrogating frequency and generating within said interrogation zone said electromagnetic interrogating field having said preselected interrogating frequency modulated as a series of pulses, and a field-changing means for varying at least one of the amplitude and direction of said electromagnetic interrogating field to alter the electromagnetic dipole coupling between said marker element and said interrogating field, said field-generating means comprising a plurality of antenna elements and said field-changing means comprising a switching system that connects a preselected one or more of said antenna elements to said frequency-generating means with a preselected polarity for each element;

a detecting means for detecting said ring-down between said pulses, said detecting means comprising a detecting antenna, an antenna-changing means, and a detector circuit connected to said detecting antenna, said detecting antenna receiving said marker dipole field and comprising at least one selectively activatable receiver element and said antenna-changing means comprising means for moving said at least one receiver element to change at least one of the position and orientation of said receiver element relative to said marker, thereby to alter the electromagnetic dipole coupling between said receiver element and said marker, the means for moving said at least one receiver element comprising at least one of a mechanical, electrical, or pneumatic element or a combination thereof; and an indication means activated by said detecting means in response to the detection of the presence of said ring-down of said marker.

2. A system as recited by claim 1, wherein said marker comprises:
a. at least one magnetomechanical element having a mechanical resonant frequency substantially equal to said preselected interrogating frequency;
b. a biasing means for magnetically biasing said magnetomechanical element; and
c. a housing enclosing said magnetomechanical element and said bias means, wherein said magnetomechanical element is free to mechanically vibrate.

3. A system as recited by claim 1, wherein said marker comprises:
a. an electrical circuit having an electrical resonant frequency substantially equal to said preselected interrogating frequency; and
b. a housing enclosing said electrical circuit.

4. A system, as recited by claim 1, wherein said marker comprises:
a. a piezoelectric element having a mechanical resonant frequency substantially equal to said preselected interrogating frequency;
b. a coil terminating across the terminals of said piezoelectric element; and
c. a housing enclosing said piezoelectric element and coil.

5. A system as recited by claim 1, wherein said field-generating means comprises at least one antenna element and said field-changing means comprises means for moving said at least one antenna element to change at least one of the position and orientation thereof.

6. In a system for detecting in human or animal tissue a surgical implement used during an operating procedure carried out in an operating room wherein a marker attached to said surgical implement changes its impedance at a preselected interrogating frequency in the presence of an electromagnetic interrogating field which provides said marker with signal-identifying characteristics, the improvement wherein:

said marker comprises at least one marker element adapted to undergo resonance at a preselected resonant frequency and radiate a marker dipole field in response to said interrogating field; said signal-identifying characteristic is a ring-down of said dipole field; the surgical implement is deployed within the wound during the operating procedure and said signal-identifying characteristics are detected by a freely movable, portable detection unit comprising:

an interrogating means that comprises a frequency-generating means for generating said preselected interrogating frequency, a field-generating means for receiving said preselected interrogating frequency and generating within said interrogation zone said electromagnetic interrogating field having said preselected interrogating frequency modulated as a series of pulses, and a field-changing means for varying at least one of the amplitude and direction of said electromagnetic interrogating field to alter the electromagnetic dipole coupling between said marker element and said interrogating field;

a detecting means for detecting said ring-down between said pulses, said detecting means comprising a detecting antenna, an antenna-changing means, and a detector circuit connected to said detecting antenna, said detecting antenna receiving said marker dipole field and comprising a plurality of said receiving elements and said antenna-changing means comprising a switching system that connects a preselected one or more of said receiver elements to said detector circuit with a preselected polarity for each element; and an indication means activated by said detecting means in response to the detection of the presence of said ring-down of said marker.

* * * * *